(12) United States Patent
Hampden et al.

(10) Patent No.: US 10,839,943 B2
(45) Date of Patent: Nov. 17, 2020

(54) GATHERING INFORMATION FROM A HEALTHCARE CONSUMER USING CONTEXT-BASED QUESTIONS, AND PROGRESSIVELY PRESENTING INFORMATION ASSOCIATED WITH A RANKED LIST OF SUGGESTED HEALTHCARE PROVIDERS

(71) Applicant: Amino, Inc., San Francisco, CA (US)

(72) Inventors: Mary Audrey Hampden, Alameda, CA (US); Sumul Mahendra Shah, Alameda, CA (US); Rebecca Ackermann, San Francisco, CA (US); Nicholas C. Dunkman, San Francisco, CA (US); Jorge A. Caballero, Menlo Park, CA (US); Abraham M. Othman, San Francisco, CA (US); David A. Vivero, San Francisco, CA (US)

(73) Assignee: Amino, Inc., San Francisco, CA (US)

(*) Notice: Subject to any disclaimer, the term of this patent is extended or adjusted under 35 U.S.C. 154(b) by 1233 days.

(21) Appl. No.: 14/885,895

(22) Filed: Oct. 16, 2015

(65) Prior Publication Data

US 2017/0061101 A1 Mar. 2, 2017

Related U.S. Application Data

(60) Provisional application No. 62/213,061, filed on Sep. 1, 2015.

(51) Int. Cl.
*G06Q 50/00* (2012.01)
*G16H 10/20* (2018.01)
(Continued)

(52) U.S. Cl.
CPC .............. *G16H 10/20* (2018.01); *G06Q 50/22* (2013.01); *G16H 10/60* (2018.01); *G16H 50/70* (2018.01)

(58) Field of Classification Search
CPC .............................. G06Q 50/22; G16H 10/20
(Continued)

(56) References Cited

U.S. PATENT DOCUMENTS 5,953,704 A * 9/1999 McIlroy ................ G06F 19/325
705/2
8,103,524 B1 1/2012 Rogers et al.
(Continued)

OTHER PUBLICATIONS

International Search Report and Written Opinion dated Jun. 29, 2016, for International Patent Application No. PCT/US2016/025353 filed Mar. 31, 2016, 14 pages.
(Continued)

*Primary Examiner* — Jonathan Ng
(74) *Attorney, Agent, or Firm* — Perkins Coie LLP

(57) ABSTRACT

Introduced are methods and systems for gathering information from a healthcare consumer using context-based questions, and progressively presenting information associated with a ranked list of suggested healthcare providers. First, the server gathers information associated with the healthcare consumer using context-based questions. Each question is formulated based on the answers the healthcare consumer has provided to previous questions, so that minimal and necessary questions are asked. Second, the server progressively sends to a healthcare consumer device, information associated with a ranked list of suggested healthcare providers. The first information tier sent to the healthcare consumer device includes a graphic representing the match strength between the healthcare consumer and the healthcare provider, and the number of similar healthcare consumers
(Continued)

the healthcare provider has treated. Based on the healthcare consumer interest, the server displays additional information to the healthcare consumer.

19 Claims, 14 Drawing Sheets

(51) Int. Cl.
  *G06Q 50/22* (2018.01)
  *G16H 10/60* (2018.01)
  *G16H 50/70* (2018.01)

(58) Field of Classification Search
  USPC .............................................. 705/2
  See application file for complete search history.

(56) References Cited

U.S. PATENT DOCUMENTS

| | | | | |
|---|---|---|---|---|
| 2002/0035486 | A1* | 3/2002 | Huyn | G06F 19/3418 705/3 |
| 2009/0179381 | A1* | 7/2009 | Menkin | A63F 1/00 273/299 |
| 2010/0010913 | A1* | 1/2010 | Pinckney | G06N 20/00 705/26.1 |
| 2010/0106518 | A1* | 4/2010 | Kuo | G16H 40/20 705/2 |
| 2010/0235295 | A1 | 9/2010 | Zides et al. | |
| 2011/0251848 | A1 | 10/2011 | Alameddine et al. | |
| 2012/0116985 | A1* | 5/2012 | Rastogi | G06Q 30/018 705/317 |
| 2013/0096937 | A1* | 4/2013 | Campbell | G06F 19/32 705/2 |
| 2013/0325509 | A1 | 12/2013 | McCarrick | |
| 2014/0180802 | A1* | 6/2014 | Boal | G06Q 30/0245 705/14.49 |
| 2015/0052160 | A1 | 2/2015 | Hussam et al. | |
| 2015/0278222 | A1* | 10/2015 | Claussenelias | G06F 16/24578 707/723 |

OTHER PUBLICATIONS

International Search Report and Written Opinion dated Jun. 24, 2016, for International Patent Application No. PCT/US2016/025373 filed Mar. 31, 2016, 14 pages.

* cited by examiner

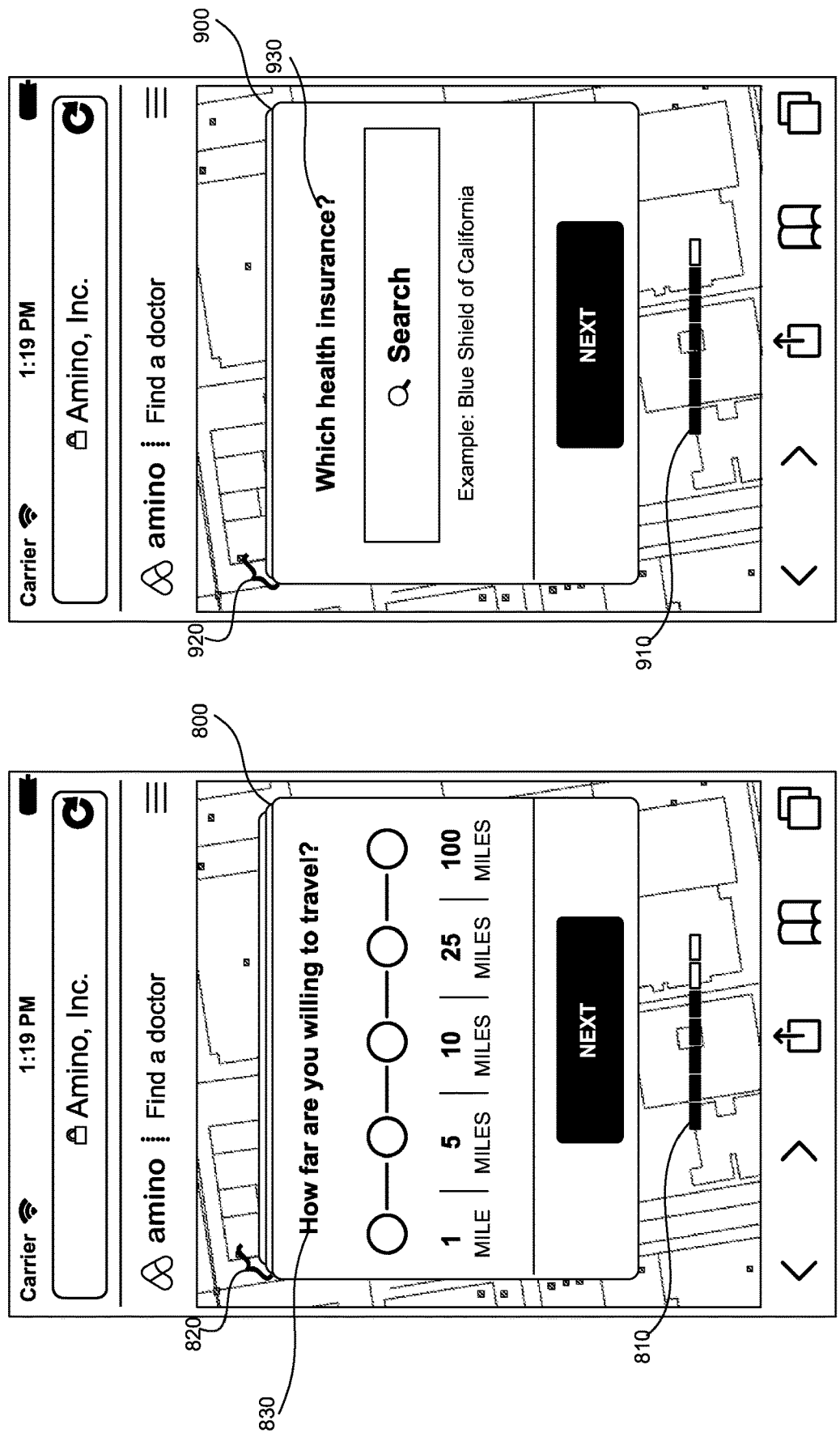

FIG. 18

GATHERING INFORMATION FROM A HEALTHCARE CONSUMER USING CONTEXT-BASED QUESTIONS, AND PROGRESSIVELY PRESENTING INFORMATION ASSOCIATED WITH A RANKED LIST OF SUGGESTED HEALTHCARE PROVIDERS

CROSS-REFERENCE TO RELATED APPLICATIONS

This application claims priority to the U.S. provisional patent application Ser. No. 62/213,061, filed Sep. 1, 2015 incorporated herein in its entirety and by this reference thereto.

TECHNICAL FIELD

Various embodiments relate generally to graphical user interfaces, more specifically to healthcare consumer interfaces for gathering information from a healthcare consumer using context-based questions, and progressively presenting information associated with a ranked list of suggested healthcare providers.

BACKGROUND

Matching healthcare providers and consumers is difficult due to the many factors that influence the quality of the match. This difficulty manifests itself in gathering sufficient information from a healthcare consumer to make a meaningful match, and in presenting information associated with a healthcare provider, in an easy to understand way.

SUMMARY

Presented here is a computer implemented method for enabling a consumer device associated with a consumer to control and interface with a remote healthcare database and a remote healthcare server, while preserving healthcare consumer privacy. The system maintains the healthcare database, which includes a healthcare provider information associated with the healthcare provider. The system instantiates a healthcare provider discovery process on the healthcare server, and a healthcare consumer discovery graphical user interface on the consumer device. Once a connection between the consumer device and the healthcare server is established, the system uses a graphical user interface on the consumer device, to enable the consumer to interact with the healthcare database. The healthcare server causes the consumer device to display a sequence of context-based questions formulated to gather only minimal and necessary information. Upon receiving the consumer responses, the healthcare server computes a ranked list of suggested healthcare providers. The server causes the consumer device to display the ranked list of suggested healthcare providers, which includes a plurality of items representing a summary of information associated with a healthcare provider. Based on healthcare consumer input, the server causes the consumer device to progressively display additional detailed information associated with a selected healthcare provider.

BRIEF DESCRIPTION OF THE DRAWINGS

These and other objects, features and characteristics of the present embodiments will become more apparent to those skilled in the art from a study of the following detailed description in conjunction with the appended claims and drawings, all of which form a part of this specification. While the accompanying drawings include illustrations of various embodiments, the drawings are not intended to limit the claimed subject matter.

FIGS. 4-10 are cards containing prompts for the consumer, according to one embodiment.

FIG. 18 is a second information tier, according to one embodiment.

DETAILED DESCRIPTION

Figure 1:
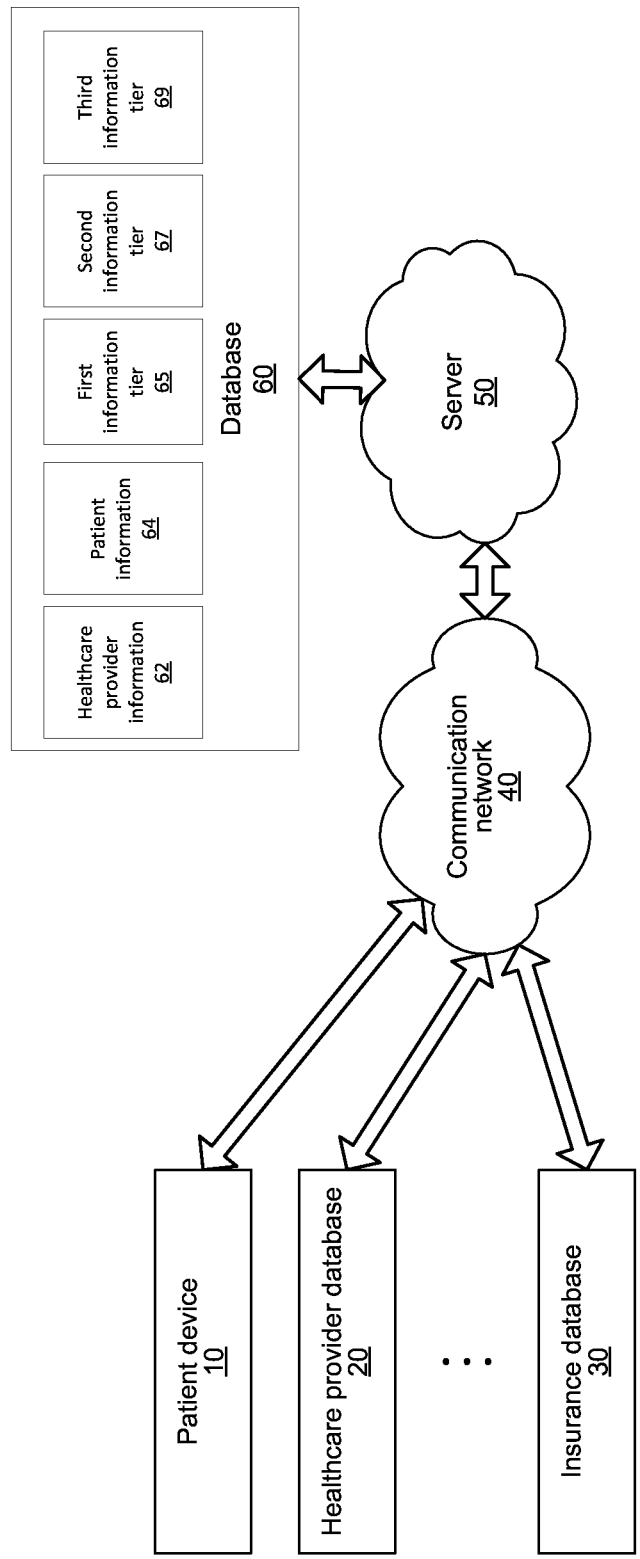
FIG. 1 is a diagram of a system for gathering information from a healthcare consumer, and progressively displaying additional information associated with a ranked list of suggested healthcare providers, according to various embodiments in the disclosure.

In the following description, for the purposes of explanation, numerous specific details are set forth in order to provide a thorough understanding of the embodiments of the invention. One skilled in the art will recognize that the embodiments of the invention may be practiced without these specific details or with an equivalent arrangement. In other instances, well-known structures and devices are shown in block diagram form in order to avoid unnecessarily obscuring the embodiments of the invention.

TERMINOLOGY

Brief definitions of terms, abbreviations, and phrases used throughout this application are given below.

In this specification, the terms "healthcare consumer," "consumer," and "healthcare consumer" are synonymous;

these terms can mean a person who has visited a healthcare provider, or a person who is a healthcare consumer of the system disclosed here. The term "healthcare server" and "server" are synonymous. The term healthcare provider comprises: doctor, nurse practitioner, physician's assistant, physical therapist, massage therapist, acupuncturist, chiropractor, herbalist, facility, practice group, or medical center. The term health issue comprises: condition, treatment, procedure, test, drug, specialty, facility, insurance, or symptom.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described that may be exhibited by some embodiments and not by others. Similarly, various requirements are described that may be requirements for some embodiments but not others.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements. The coupling or connection between the elements can be physical, logical, or a combination thereof. For example, two devices may be coupled directly, or via one or more intermediary channels or devices. As another example, devices may be coupled in such a way that information can be passed there between, while not sharing any physical connection with one another. Additionally, the words "herein," "above," "below," and words of similar import, when used in this application, shall refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

If the specification states a component or feature "may," "can," "could," or "might" be included or have a characteristic, that particular component or feature is not required to be included or have the characteristic.

The term "module" refers broadly to software, hardware, or firmware components (or any combination thereof). Modules are typically functional components that can generate useful data or another output using specified input(s). A module may or may not be self-contained. An application program (also called an "application") may include one or more modules, or a module may include one or more application programs.

The terminology used in the Detailed Description is intended to be interpreted in its broadest reasonable manner, even though it is being used in conjunction with certain examples. The terms used in this specification generally have their ordinary meanings in the art, within the context of the disclosure, and in the specific context where each term is used. For convenience, certain terms may be highlighted, for example using capitalization, italics, and/or quotation marks. The use of highlighting has no influence on the scope and meaning of a term; the scope and meaning of a term is the same, in the same context, whether or not it is highlighted. It will be appreciated that the same element can be described in more than one way.

Consequently, alternative language and synonyms may be used for any one or more of the terms discussed herein, but special significance is not to be placed upon whether or not a term is elaborated or discussed herein. A recital of one or more synonyms does not exclude the use of other synonyms. The use of examples anywhere in this specification, including examples of any terms discussed herein, is illustrative only and is not intended to further limit the scope and meaning of the disclosure or of any exemplified term. Likewise, the disclosure is not limited to various embodiments given in this specification.

Overview

Presented here is a computer implemented method for enabling a consumer device associated with a healthcare consumer to control and interface with a remote healthcare database and a remote healthcare server, while preserving healthcare consumer privacy. The system maintains the healthcare database, which includes a healthcare provider information associated with the healthcare provider. The system instantiates a healthcare discovery process on the healthcare server, and a healthcare consumer discovery graphical user interface on the consumer device. Once a connection between the consumer device and the healthcare server is established, the system uses a graphical user interface on the consumer device, to enable the consumer to interact with the healthcare database. The healthcare server causes the consumer device to display a sequence of context-based questions formulated to gather only minimal and necessary information. Upon receiving the consumer responses, the healthcare server computes a ranked list of suggested healthcare providers. The server causes the consumer device to display the ranked list of suggested healthcare providers, which includes a plurality of items representing a summary of information associated with a healthcare provider. Based on consumer input, the server causes the consumer device to progressively display additional detailed information associated with a selected healthcare provider.

FIG. 1 is a diagram of a system for gathering information from a consumer, and progressively displaying additional information associated with a ranked list of suggested healthcare providers, according to various embodiments in the disclosure. One or more consumer devices associated with a consumer 10 connect to a server 50 via a communication network 40. One or more databases associated with a healthcare provider 20, and one or more databases associated with insurance provider 30 connect to server 50 via a communication network 40. The insurance provider database 50 can contain information regarding the claims submitted to the insurance provider. The server 50 can store the data it receives from the healthcare consumer device 10, and databases 20, 30 into the database 60. In another embodiment, the server 50 can store the data it receives from databases 20, 30 into the database 60. The server 50 analyzes the received data and stores the received data into at least the following data sets: healthcare provider information 62, first information tier 65, and second information tier 67. The server 50 can also store healthcare consumer information 64, and an arbitrary number of information tiers, such as third information tier 69. Various information tiers 65, 67, 69 can contain unique data, or can contain overlapping data.

Figure 2:
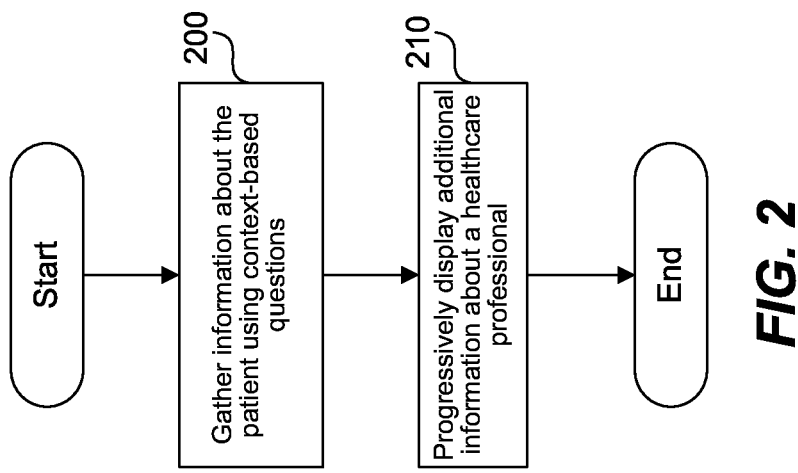
FIG. 2 is a flowchart of steps taken by the server in gathering and displaying information, according to one embodiment.
Figure 3:
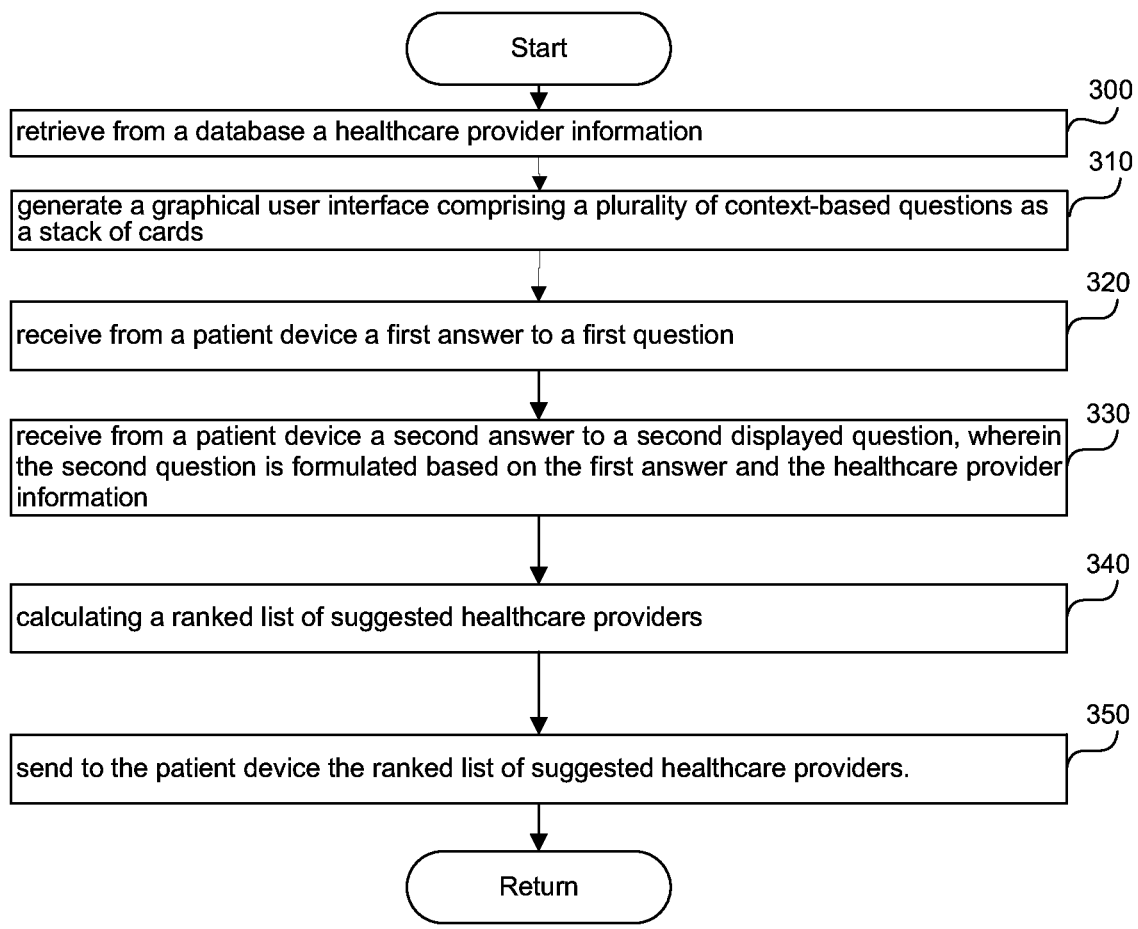
FIG. 3 is a flowchart of steps taken by the server 50 in gathering consumer information, according to one embodiment.
Figure 4:
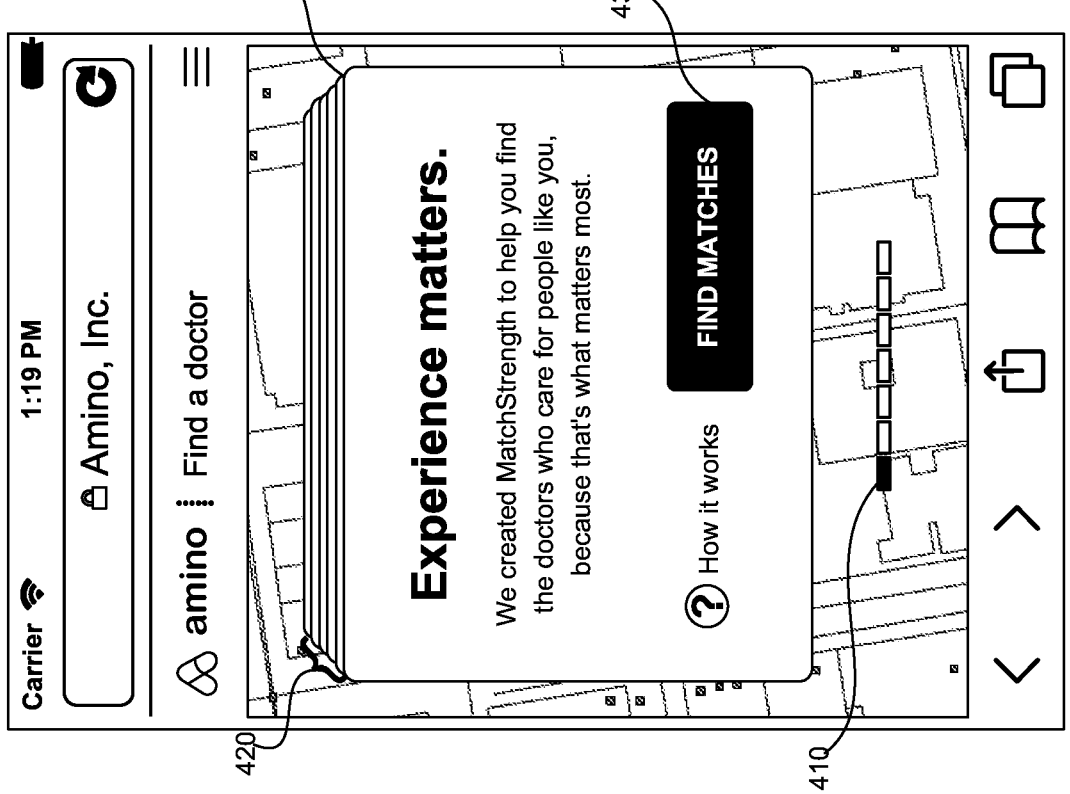

The server 50 can use healthcare provider information 62, or healthcare consumer information 64, or both, in formulating questions, and suggested responses, to present to the consumer, in at least step 200 of FIG. 2, step 320 of FIG. 3, and step 410 of FIG. 4. The server 50 calculates a ranked list of suggested healthcare providers, 1300 in FIG. 13, to send to the consumer device 10.

The consumer device 10, and databases 20, 30, 60 and the server 50, communicate with each other and other components of the communication network 40 using well known, new, or still developing protocols. In this context, a protocol includes a set of rules defining how the network nodes within the communication network 40 interact with each other based on information sent over the communication links.

By way of example, the communication network 40 includes one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network (e.g., a proprietary cable or fiber-optic network, and the like, or any combination thereof). In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

The databases 20, 30, 60 can be stored on an Internet node, a server, a cloud, fixed terminal, station, unit, device, multimedia computer, desktop computer, laptop computer, notebook computer, netbook computer, tablet computer, or any combination thereof.

The consumer device 10 can be any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, the accessories and peripherals of these devices, or any combination thereof.

FIG. 2 is a flowchart of steps taken by the server 50 in gathering and displaying information, according to one embodiment. In step 200, the server 50 gathers information associated with the consumer using context-based questions. In step 210, the server 50 progressively sends to the consumer device 10 information associated with a ranked list of suggested healthcare providers, 1300 in FIG. 13.

Context-Based Questions

FIG. 3 is a flowchart of steps taken by the server 50 in gathering consumer information, according to one embodiment. In step 300, the server 50 retrieves from the database 60 healthcare provider information 62. The healthcare provider information 62 can contain information regarding the claims submitted to an insurance provider, healthcare consumers treated, address associated with the healthcare consumers treated, distance a healthcare consumer associated with a healthcare provider travels to meet with the healthcare provider, procedures performed, healthcare provider education, healthcare provider contact information, etc.

According to another embodiment, the server 50 can receive login information associated with a consumer from the consumer device 10. Based on the login information, the server 50 can retrieve from the database 60 healthcare consumer information 64 associated with a healthcare consumer. The healthcare consumer information 64 can include: a healthcare consumer profile; medical history associated with the healthcare consumer; recent health issues associated with a healthcare consumer etc. The healthcare consumer profile associated with the healthcare consumer includes all the answers the healthcare consumer has previously entered into the system, while logged in. According to one embodiment, the server 50 can store the healthcare consumer answers to the questions presented in the healthcare consumer profile, and store the healthcare consumer profile with the healthcare consumer information 64 in database 60.

According to one embodiment, in order to secure consumer's privacy, consumer answers to the context-based questions are deleted when there are no longer needed, such as after the ranked list of suggested healthcare providers is generated, or after the consumer books an appointment.

Figure 5:
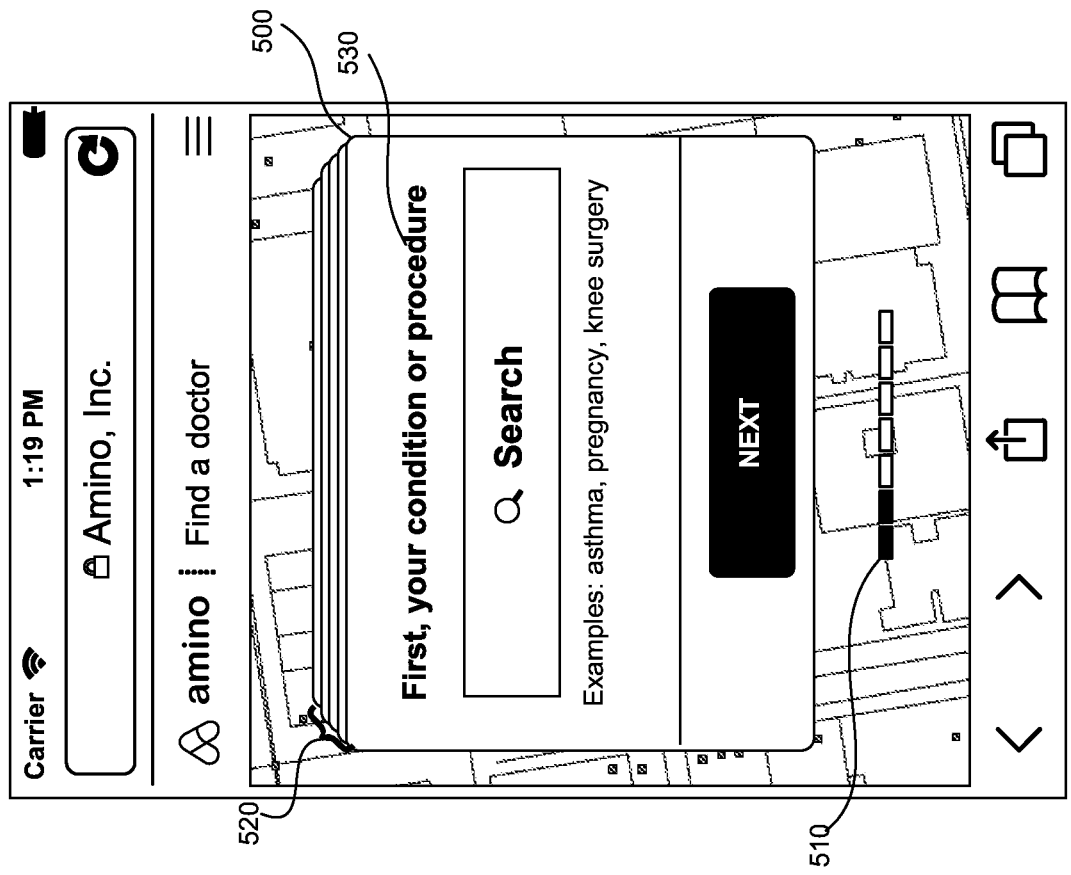
Figure 7:
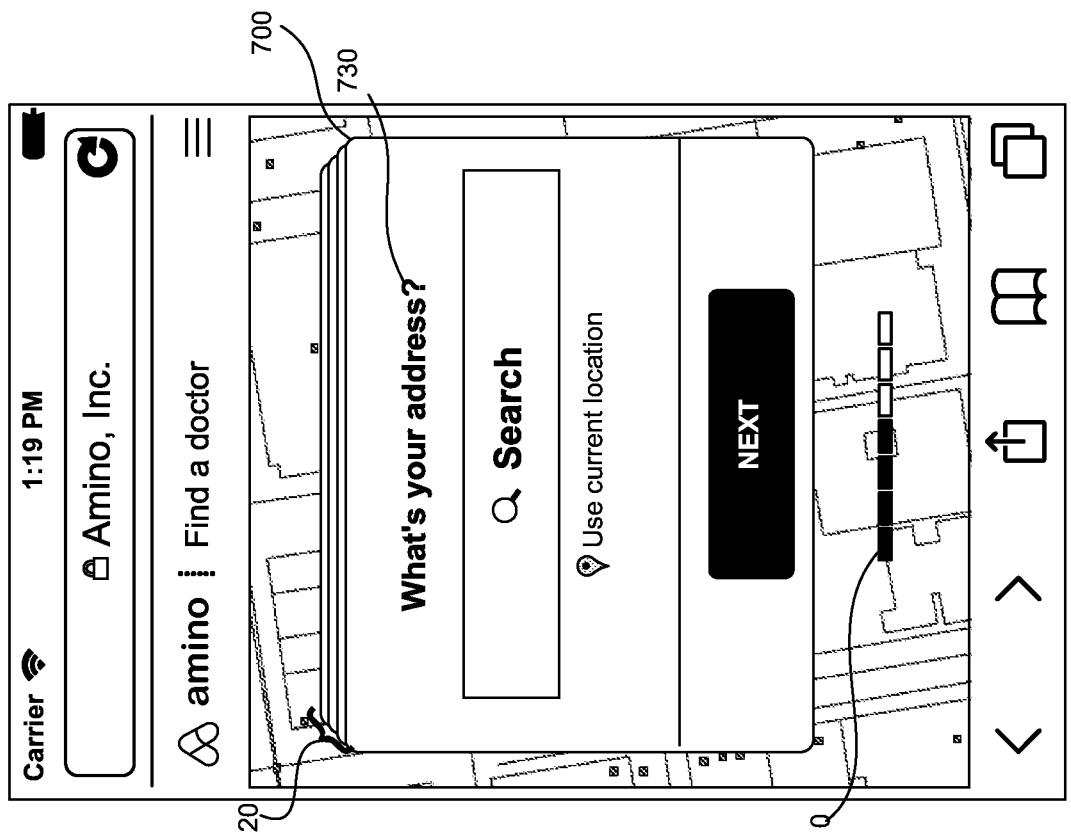
Figure 6:
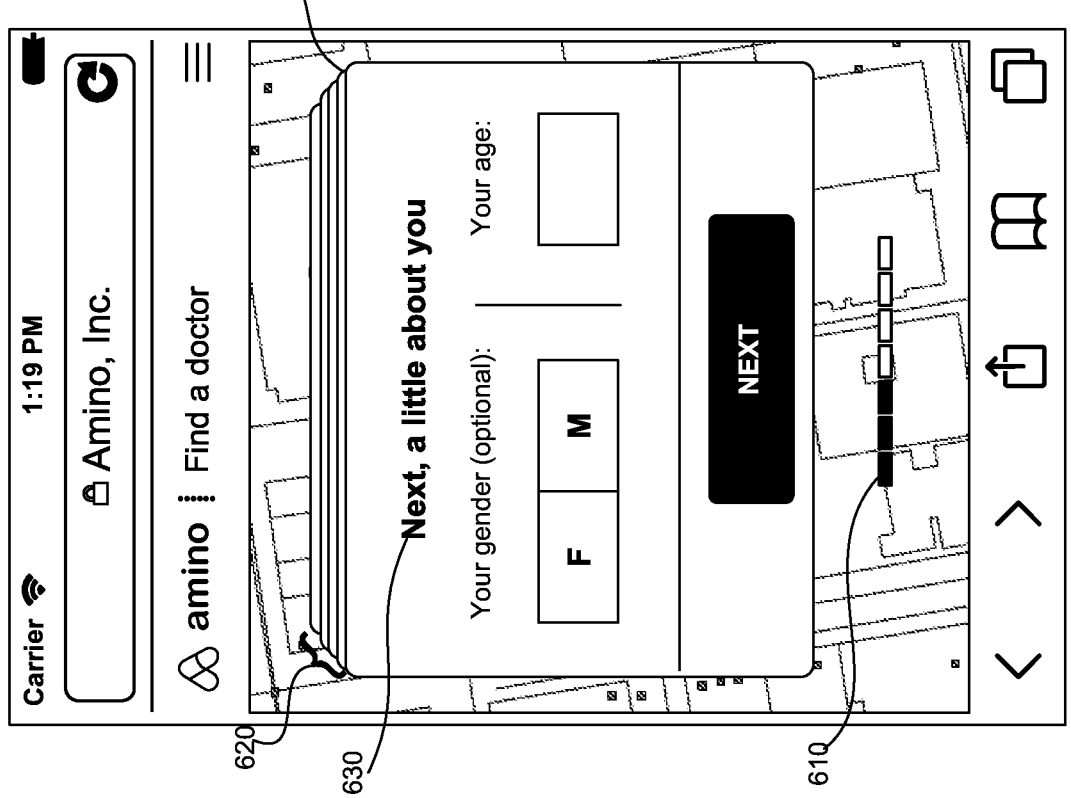
Figure 10:
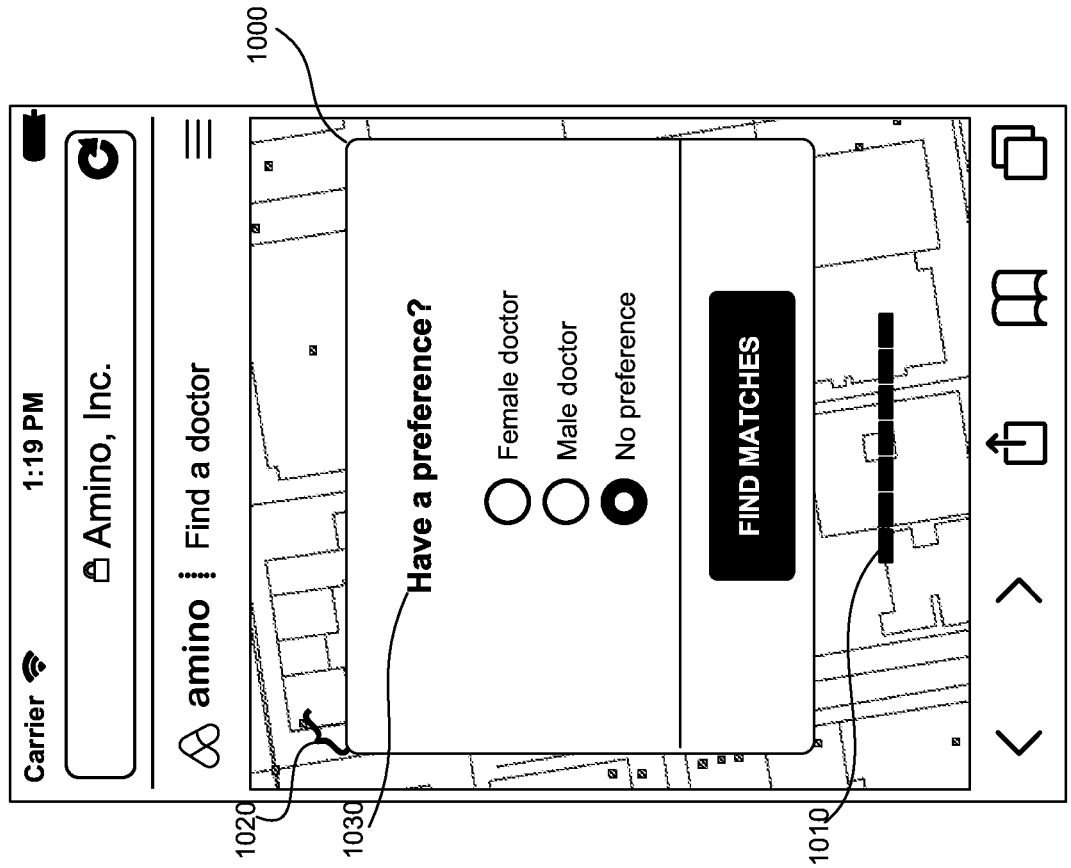

In step 310, the server 50 generates a graphical user interface comprising a plurality of context-based questions as a stack of cards. Each card in the stack of cards is associated with a single question. Elements, 420 in FIG. 4, 520 in FIG. 5, 620 in FIG. 6, 720 in FIG. 7, 820 in FIG. 8, 920 in FIG. 9, 1020 in FIG. 10 are an indication of a number of questions remaining, displayed as a stack of partially visible cards. The sequence of context-based questions is formulated to gather only minimal and necessary information, such as: a health issue associated with a healthcare consumer, an age associated with a healthcare consumer, a distance the healthcare consumer is willing to travel, a health insurance associated with a healthcare consumer, and a healthcare consumer preference regarding the gender of the healthcare provider. Each subsequent question in the sequence of context-based questions is formulated based on the previously received answers.

In step 320, the server 50 receives from a consumer device 10 associated with a consumer, a first answer to a first displayed question. According to one embodiment, such as FIG. 5, the first question asks the consumer to specify the health issue for which the consumer is seeking treatment. According to another embodiment, the server 50 formulates the first question based on the consumer information 64, such as recent health issues associated with a consumer.

Figure 11:
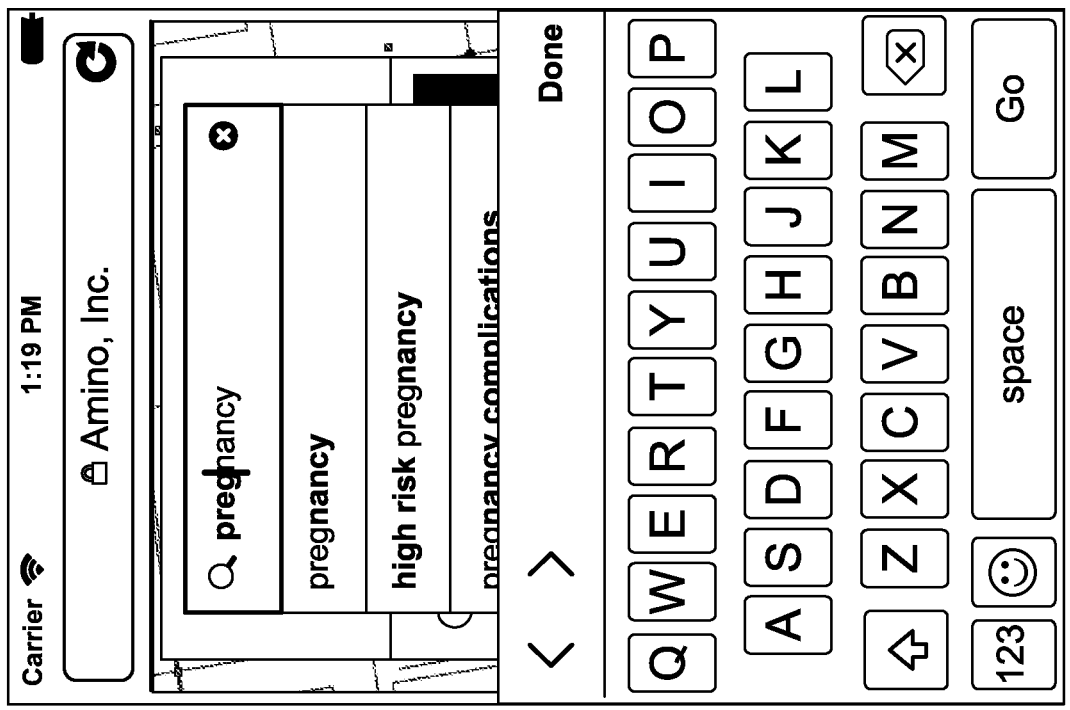
FIG. 11 is a list of suggested answers to a consumer question, according to one embodiment.

According to one embodiment, the server 50 can suggest a list of likeliest answers to the first question, such as FIG. 11. For example, the server 50 can suggest a list of likeliest health issues based on recent health issues associated with the healthcare consumer, or based on healthcare provider information, and healthcare consumer information.

According to another embodiment, the server 50 can also receive geolocation information associated with the healthcare consumer device 10. Based on the geolocation information, and the healthcare provider information 62, the server 50, can suggest a list of likeliest health issues. For example, if the geographic area where the healthcare consumer device is located, such as a city, a county, or a state, is undergoing an influenza epidemic, the server 50 would suggest influenza as a health issue.

In another embodiment, the server 50 can narrow down the suggested health issues based on the alphanumeric characters received from the healthcare consumer device. For example, when the healthcare consumer types alphanumeric characters "preg", the server 50 suggests "pregnancy", "high risk pregnancy", or "pregnancy complications", etc., as a list of likeliest answers to the question.

In step 330, the server 50 receives from a healthcare consumer device 10, a second answer to a second displayed question. The server 50 formulates the second question based on the first answer and the healthcare provider information 62. For example, when the server 50 receives pregnancy as the first answer, and the healthcare provider information indicates that a C-section is a procedure performed in pregnancy, the server 50 formulates the second question to ask the consumer if the consumer is interested in having a C-section performed. According to another embodiment, the server formulates the second question based on the first answer, the healthcare provider information 62, and the consumer information 64. For example, when the server 50 receives pregnancy as the first answer, the healthcare provider information indicates that a C-section is a procedure performed in pregnancy, and the consumer information 64 indicates that the consumer is not interested in having a C-section performed, the server 50 formulates the second question to ask the consumer about other information, such as whether the consumer has a preference for a gender of the healthcare provider.

The questions presented to the healthcare consumer include questions regarding the health issue associated with a healthcare consumer, healthcare consumer gender, healthcare consumer age, a distance the healthcare consumer is willing to travel, healthcare consumer address, healthcare consumer health insurance, and healthcare consumer preference for the healthcare provider gender.

Figure 13:
FIG. 13 is a ranked list of suggested healthcare providers, according to one embodiment.

In step 340, the server 50 calculates a ranked list of suggested healthcare providers, 1300 in FIG. 13, based on the answers the server 50 received from the healthcare consumer device 10, and based on the healthcare provider information. For example, the ranked list of suggested healthcare providers 1300 contains healthcare providers that accept healthcare consumer health insurance. The ranked list 1300 is ordered from the provider with the highest match strength to the healthcare consumer, to the provider with the lowest match strength to the healthcare consumer. The match strength is based on the number of similar healthcare consumers the healthcare provider has treated. According to one embodiment, similar healthcare consumers are healthcare consumers of similar age as the current healthcare consumer, healthcare consumers of same gender as the current healthcare consumer, and healthcare consumers with a related health issue as the current healthcare consumer. According to another embodiment, when the healthcare consumer does not specify the gender, similar healthcare consumers are healthcare consumers of similar age as the current healthcare consumer and healthcare consumers with a related health issue as the current healthcare consumer.

Similar age is determined based on the health issue associated with the healthcare consumer and healthcare consumer age. The server 50 uses a mathematical technique called B-splines to smooth healthcare consumer ages. The set of B-splines, the server 50 uses, is adaptive and changes for each condition, procedure, and specialty. For some conditions, a 32-year-old woman and a 45-year-old woman have similar concerns and will see similar doctors. But for others, like pregnancy, those women will have different concerns and may see different doctors. For each condition and specialty the algorithms use data stored in database 60 to learn how similar healthcare consumers of different ages are.

A related health issue is a health issue that has similar symptoms, a health issue for which similar procedures are performed, a health issue for which similar treatments are prescribed, a health issue for which similar drugs are prescribed, or a health issue for which similar tests are performed. For example, when a healthcare consumer searches for pregnancy as the health issue, a related health issue is a C-section.

In step 350, the server 50 sends to the consumer device 10 the ranked list of suggested healthcare providers, 1300 in FIG. 13, the ranked list including a graphic representing a match strength between the healthcare consumer and the healthcare provider, and a text representing a number of similar healthcare consumers the healthcare provider has treated. In another embodiment, the ranked list includes a graphic comparison between a frequency associated with a relevant procedure performed by the healthcare provider and an average frequency associated with the relevant procedure performed by other healthcare providers, or the ranked list includes a graphic badge indicating that the healthcare provider treats more healthcare consumers than 99% of other healthcare providers in the same specialty. Other healthcare providers can be the other healthcare providers in the ranked list 1300, or other healthcare providers in a healthcare consumer-defined search radius, or other healthcare providers the same city, ZIP code, county, state, or country, as a selected healthcare provider. The relevant procedure includes a procedure associated with the healthcare consumer health issue. For example, when the healthcare consumer health issue is pregnancy, the relevant procedure can be a C-section. When the healthcare consumer health issue is a repetitive stress injury, the relevant procedure can be a carpal tunnel surgery. The frequency associated with the relevant procedure is calculated with respect to a risk-adjusted group of healthcare consumers. For example, if the health issue is pregnancy, and the age of the mother is over 35, the graphic will compare the frequency of C-sections in the healthcare consumer population over 35 years of age.

FIGS. 4-10 are cards containing prompts for the healthcare consumer, according to one embodiment. Each card 400 in FIG. 4, 500 in FIG. 5, 600 in FIG. 6, 700 and FIG. 7, 800 in FIG. 8, 900 in FIG. 9, 1000 in FIG. 10, contains a prompt 430 in FIG. 4, 530 in FIG. 5, 630 in FIG. 6, 730 in FIG. 7, 830 in FIG. 8, 930 in FIG. 9, 1030 in FIG. 10. Prompt 430, when selected by the healthcare consumer, initiates the information gathering process. Prompts 530, 630, 730, 830, 930, 1030 are context-based questions, querying the healthcare consumer for relevant information. Elements, 410, 420 in FIG. 4, 510, 520 in FIG. 5, 610, 620 in FIG. 6, 710, 720 in FIG. 7, 810, 820 in FIG. 8, 910, 920 in FIG. 9, 1010, 1020 in FIG. 10 are visual guides indicating how many more questions the healthcare consumer has to answer. Elements 420, 520, 620, 720, 820, 920, 1020 are visual guides representing a deck of cards. As the number of questions remaining decreases, so does the number of cards in the deck. Elements 410, 510, 610, 710, 810, 910, 1010 are visual guides representing the number of questions remaining as empty bars, while the number of questions answered and the question currently viewed is represented by solid bars.

FIG. 11 is a list of suggested answers to a healthcare consumer question, according to one embodiment. For example, the server 50 can suggest a list of likeliest health issues based on recent health issues associated with the healthcare consumer. According to another embodiment, the server 50 can also receive geolocation information associated with the healthcare consumer device 10. Based on the geolocation information, and the healthcare provider information 62, the server 50, can suggest a list of likeliest health issues. For example, if the geographic area where the healthcare consumer device is located, such as a city, a ZIP code, a county, or a state, is undergoing an influenza epidemic, the server 50 would suggest influenza as a health issue. In another embodiment, the server 50 can narrow down the suggested health issues based on the alphanumeric characters received from the healthcare consumer device. For example, when the healthcare consumer types alphanumeric characters "preg", the server 50 suggests "pregnancy", "high risk pregnancy", or "pregnancy complications", etc., as a list of likeliest answers to the question.

Presenting Healthcare Provider Information

Figure 12:
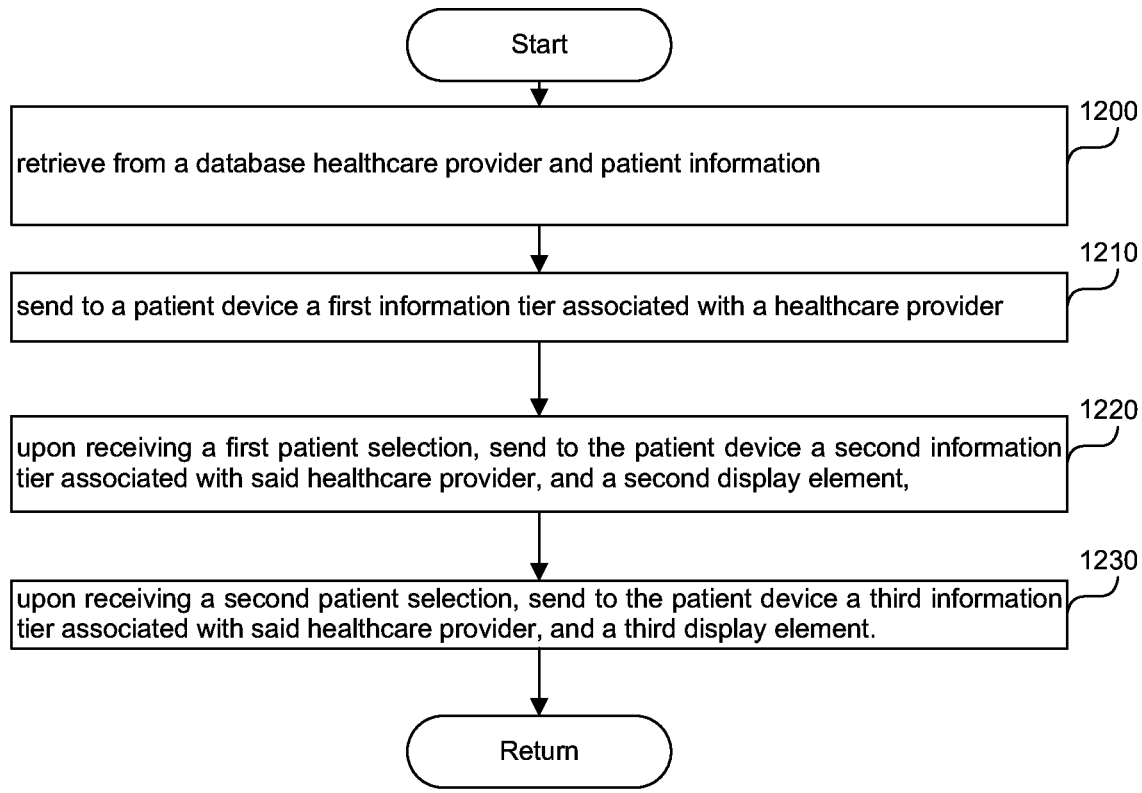
FIG. 12 is a flowchart of steps taken by the server in progressively presenting healthcare provider information, according to one embodiment.

FIG. 12 is a flowchart of steps taken by the server 50 in progressively presenting healthcare provider information, according to one embodiment. In step 1200, the server 50 receives from the database 60 information associated with a healthcare provider, and a healthcare consumer. The server 50 can also receive healthcare consumer information from the consumer device 10.

In step 1210, the server 50 sends to a consumer device 10 a ranked list of suggested healthcare providers 1300 in FIG. 13. The ranked list comprises a plurality of items representing a first information tier 65 associated with a healthcare provider, and a first display element configured to receive a first healthcare consumer selection. The first information tier 65 comprises a graphic representing a match strength between said healthcare consumer and said healthcare provider, and a text representing a number of similar healthcare consumers said healthcare provider has treated. According to one embodiment, the first display element can be an item 1360 associated with the ranked list 1300. The ranked list 1300 comprises a graphic representing a match strength between the healthcare consumer and the healthcare provider, 1310, 1320 in FIG. 13, and a text 1330 representing a number of similar healthcare consumers the healthcare provider has treated. According to one embodiment, similar healthcare consumers are healthcare consumers of similar age as the current healthcare consumer, healthcare consumers of same gender as the current healthcare consumer, and healthcare consumers with a related health issue as the current healthcare consumer. According to another embodiment, when the healthcare consumer does not specify the gender, similar healthcare consumers are healthcare consumers of similar age as the current healthcare consumer and healthcare consumers with a related health issue as the current healthcare consumer.

Similar age is determined based on the health issue associated with the healthcare consumer and healthcare consumer age. The server 50 uses a mathematical technique called B-splines to smooth healthcare consumer ages. The set of B-splines, the server 50 uses, is adaptive and changes for each condition and specialty. For some conditions, a 32-year-old woman and a 45-year-old woman have similar concerns and will see similar doctors. But for others, like pregnancy, those women will have different concerns and may see different doctors. For each condition and specialty the algorithms use data stored in database 60 to learn how similar healthcare consumers of different ages are.

A related health issue is a health issue that has similar symptoms, a health issue for which similar procedures are performed, a health issue for which similar treatments are prescribed, a health issue for which similar drugs are prescribed, or a health issue for which similar tests are performed. For example, when a healthcare consumer searches for pregnancy as the health issue, a related health issue is a C-section.

Figure 14B:
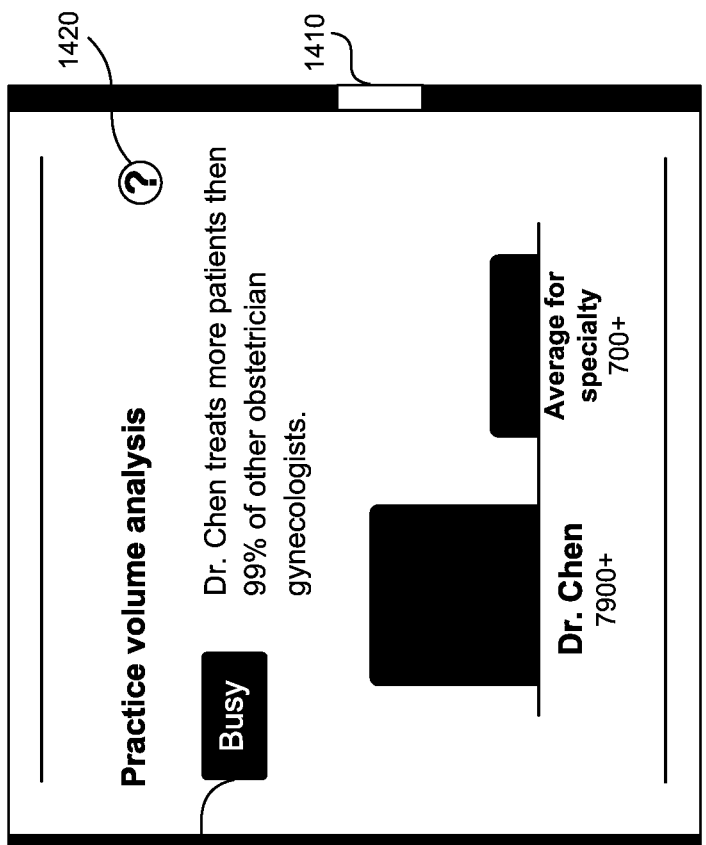
FIG. 14B is a graphic comparison between the average number of healthcare consumers the healthcare provider has treated, and an average number of healthcare consumers other healthcare providers have treated, according to one embodiment.

According to one embodiment, the first information tier 65 further comprises a graphic comparison, 1340, 1350 in FIG. 13, between a frequency associated with a relevant procedure performed by the healthcare provider and an average frequency associated with the relevant procedure performed by other healthcare providers, or the ranked list includes a graphic badge, 1430 in FIG. 14B, indicating that the healthcare provider treats more healthcare consumers than 99% of other healthcare providers in the same specialty. The frequency associated with the relevant procedure is calculated with respect to a risk adjusted group of healthcare consumers. For example, if the health issue is pregnancy, and the age of the mother is over 35, the graphic will compare the frequency of C-sections in the healthcare consumer population over 35 years of age. Other healthcare providers can be the other healthcare providers in the ranked list 1300, or other healthcare providers in a healthcare consumer-defined search radius, or other healthcare providers the same city, ZIP code, county, state, or country, as the selected healthcare provider. According to another embodiment, the ranked list 1300 further comprises a visual representation associated with a healthcare provider, such as a photograph, a logo, a video, etc.

Figure 14A:
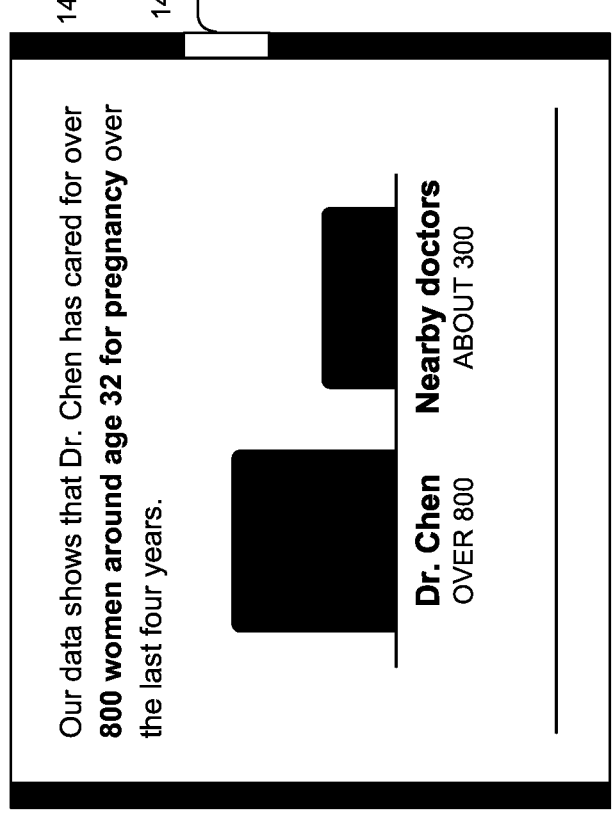
FIG. 14A is a graphic comparison between the number of similar healthcare consumers the healthcare provider has treated, and an average number of similar healthcare consumers other healthcare providers have treated, according to one embodiment.
Figure 15:
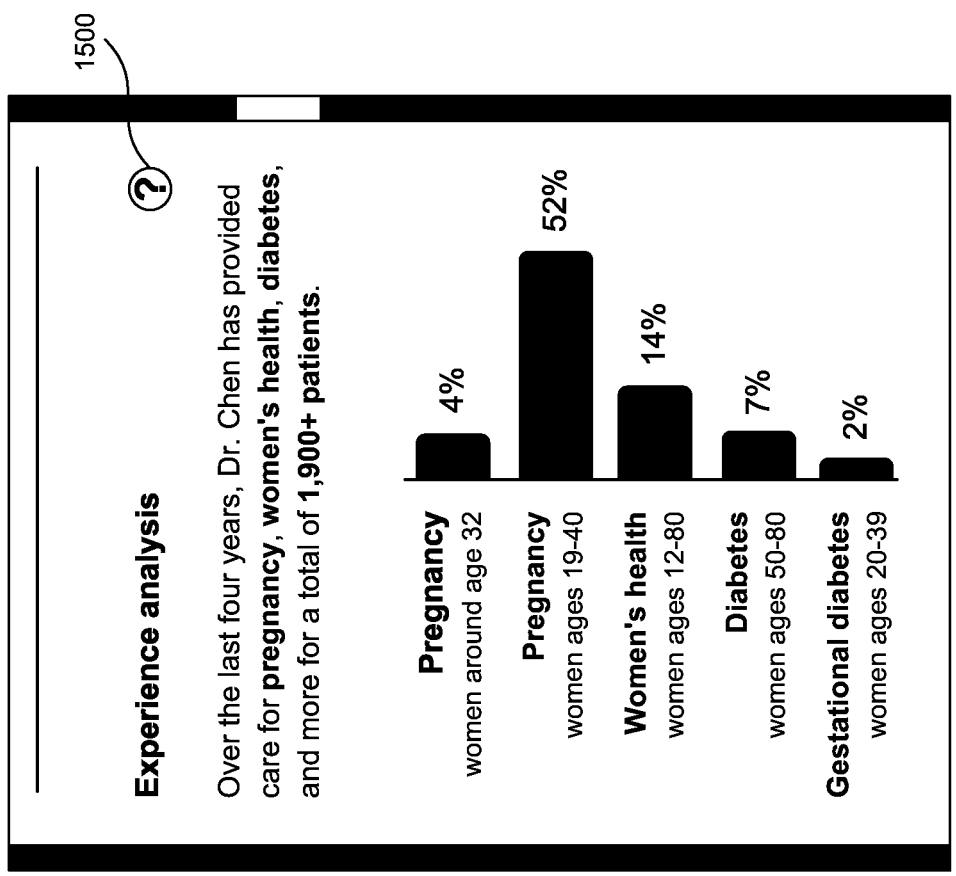
FIG. 15 is a graphic representation of a percentage breakdown of different health issues the healthcare provider has treated, according to one embodiment.

In step 1220, the server 50 upon receiving a first healthcare consumer selection, sends to the healthcare consumer device a second information tier 67 associated with the healthcare provider, and a second display element, 1400 in FIG. 14A, 1410 and 1420 in FIG. 14B, 1500 in FIG. 15, configured to receive a second healthcare consumer selection. The second information tier 67 comprises a graphic comparison between the number of similar healthcare consumers the healthcare provider has treated, and an average number of similar healthcare consumers other healthcare providers have treated. Other healthcare providers can be the other healthcare providers in the ranked list 1300, or other healthcare providers in a healthcare the consumer-defined search radius, or healthcare providers in the same city, ZIP code, county, state, or country, as a selected healthcare provide. According to one embodiment, the second information tier 67 also comprises a visual representation associated with the healthcare provider, such as a photograph, logo, video, etc.

In step 1230, upon receiving a second healthcare consumer selection, sending to the healthcare consumer device a third information tier 69 associated with the healthcare provider, and a third display element, 1400 in FIG. 14A, 1410 and 1420 in FIG. 14B, 1500 in FIG. 15 configured to receive a third healthcare consumer selection. The third information tier 69 comprises a graphic representation of a percentage breakdown of different health issues the healthcare provider has treated. According to one embodiment, third information tier further comprises success rates associated with the treatments, such as a graphic display specifying the percentage success rate associated with a procedure. In another embodiment, the 3rd information tier 69 can comprise a graphic comparison between an average number of healthcare consumers the healthcare provider treats and an average number of healthcare consumers other healthcare providers treat. Other healthcare providers can be the other healthcare providers in the ranked list 1300, or other healthcare providers in a healthcare consumer-specified search radius, or healthcare providers in the same city, ZIP code, county, state, or country, as a selected healthcare provider.

Figure 17:
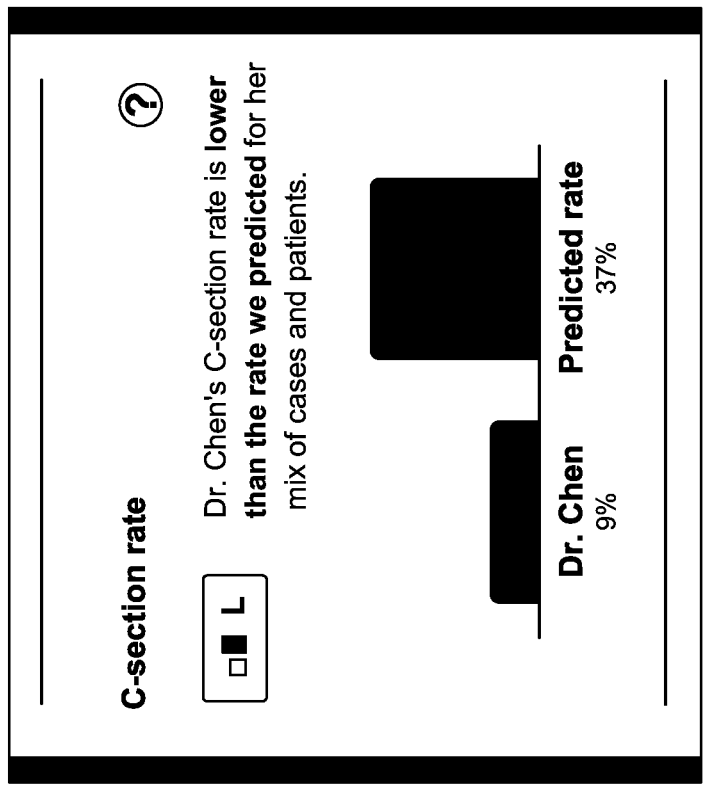
FIGS. 16-17 are a graphic comparison between the healthcare provider and other healthcare providers, according to various embodiments.
Figure 16:
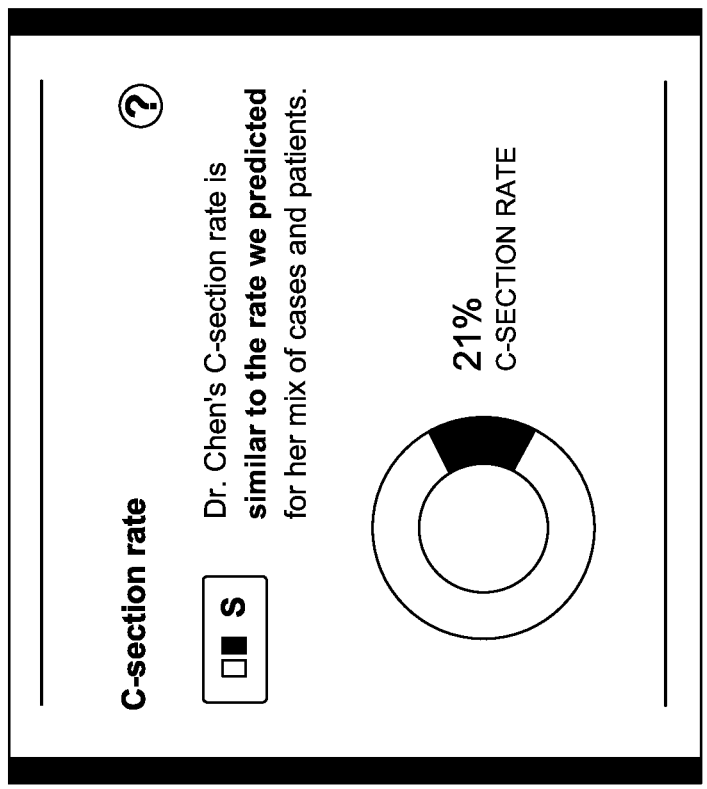

There may be an arbitrary number of information tiers. Further, different information tiers can contain overlapping information, or can contain non-overlapping information. According to one embodiment, upon receiving a third healthcare consumer selection, the server 50 sends to the healthcare consumer device a fourth information tier associated with the healthcare provider, and a fourth display element 1400 in FIG. 14A, 1410 and 1420 in FIG. 14B, 1500 and FIG. 15 configured to receive a fourth healthcare consumer selection. The fourth information tier, as illustrated in FIGS. 16-17, comprises a graphic comparison between a frequency associated with a relevant procedure performed by the healthcare provider and a predicted average frequency associated with the relevant procedure performed by other healthcare providers. FIGS. 16-17 are a graphic comparison between the healthcare provider and other healthcare providers, according to various embodiments. The other healthcare providers may be the other healthcare providers in the ranked list 1300, or other healthcare providers in a consumer provided search radius, or other healthcare providers the same city, ZIP code, county, state, or country as the selected healthcare provider. An information tier can also contain an explanation of how the system works, how the healthcare provider statistics is gathered, how the statistics is adjusted based on health risks associated with different healthcare consumer groups etc.

FIG. 13 is a ranked list of suggested healthcare providers, according to one embodiment. Elements 1310 and 1320 are a graphic representing a match strength between the healthcare consumer and the healthcare provider. The graphic element 1310 representing the first healthcare provider in the ranked list 1300 appears as a bar almost filled with a color, or a pattern. The graphic element 1320 representing subsequent healthcare providers in the ranked list 1300 appears as a bar proportionally filled with a color or a pattern. For example, when the second healthcare provider has seen half as many healthcare consumers as the first healthcare provider, the bar 1320 associated with the second healthcare provider is filled half as much as the bar 1310 associated with the first healthcare provider.

FIG. 14A is a graphic comparison between the number of similar healthcare consumers the healthcare provider has treated, and an average number of similar healthcare consumers other healthcare providers have treated, according to one embodiment. Other healthcare providers can be the other healthcare providers in the ranked list 1300, or other healthcare providers in a healthcare consumer-specified search radius, or healthcare providers in the same city, ZIP code, county, state, or country, as a selected healthcare provider. Element 1400 is a display element, configured to receive a healthcare consumer selection, according to one embodiment. In this embodiment, the display element is a sliding bar, which the healthcare consumer can slide down, if the healthcare consumer is interested in further information associated with the healthcare provider.

FIG. 14B is a graphic comparison between the average number of healthcare consumers the healthcare provider has treated, and an average number of healthcare consumers other healthcare providers have treated, according to one embodiment. Element 1430 indicates that the healthcare provider treats more healthcare consumers than 99% of other healthcare providers in the same specialty. In some embodiments, the first information tier 65 can comprise element 1430. Other healthcare providers can be the other healthcare providers in the ranked list 1300, or other healthcare providers in a healthcare consumer-specified search radius, or healthcare providers in the same city, ZIP code, county, state, or country, as a selected healthcare provider.

Elements 1410, and 1420 are display elements configured to receive a healthcare consumer selection, according to one embodiment. In this embodiment, the display element 1410 is a sliding bar, which the healthcare consumer can slide down, if the healthcare consumer is interested in further information associated with the healthcare provider. The display element 1420 is an icon, which, upon selection, displays additional information associated with a healthcare provider to the healthcare consumer. According to one embodiment, the additional information explains how the percentage breakdown was computed, the risk factors associated with the healthcare consumers the healthcare provider has treated, how the other healthcare providers are selected, etc.

FIG. 15 is a graphic representation of a percentage breakdown of different health issues the healthcare provider has treated, according to one embodiment. Element 1500 is a display element, configured to receive a healthcare consumer selection, according to one embodiment. In this embodiment, the display element is an icon, which, upon selection, displays additional information associated with a healthcare provider to the healthcare consumer. According to one embodiment, the additional information explains how the percentage breakdown was computed, the risk factors associated with the healthcare consumers the healthcare provider has treated, how the other healthcare providers are selected, etc.

FIGS. 16-17 are a graphic comparison between procedure rates associated with a healthcare provider and predicted procedure rates, according to various embodiments. The predicted procedure rate can be an average rate associated with other healthcare providers who have treated a corresponding risk-adjusted group of healthcare consumers. For example, when the health issue is pregnancy, and the age of the mother is over 35, the corresponding risk-adjusted group of healthcare consumers is a healthcare consumer population over 35 years of age. The other healthcare providers may be the other healthcare providers in the ranked list 1300, or other healthcare providers in the same city, county, state, country as the selected healthcare provider.

Figure 18:
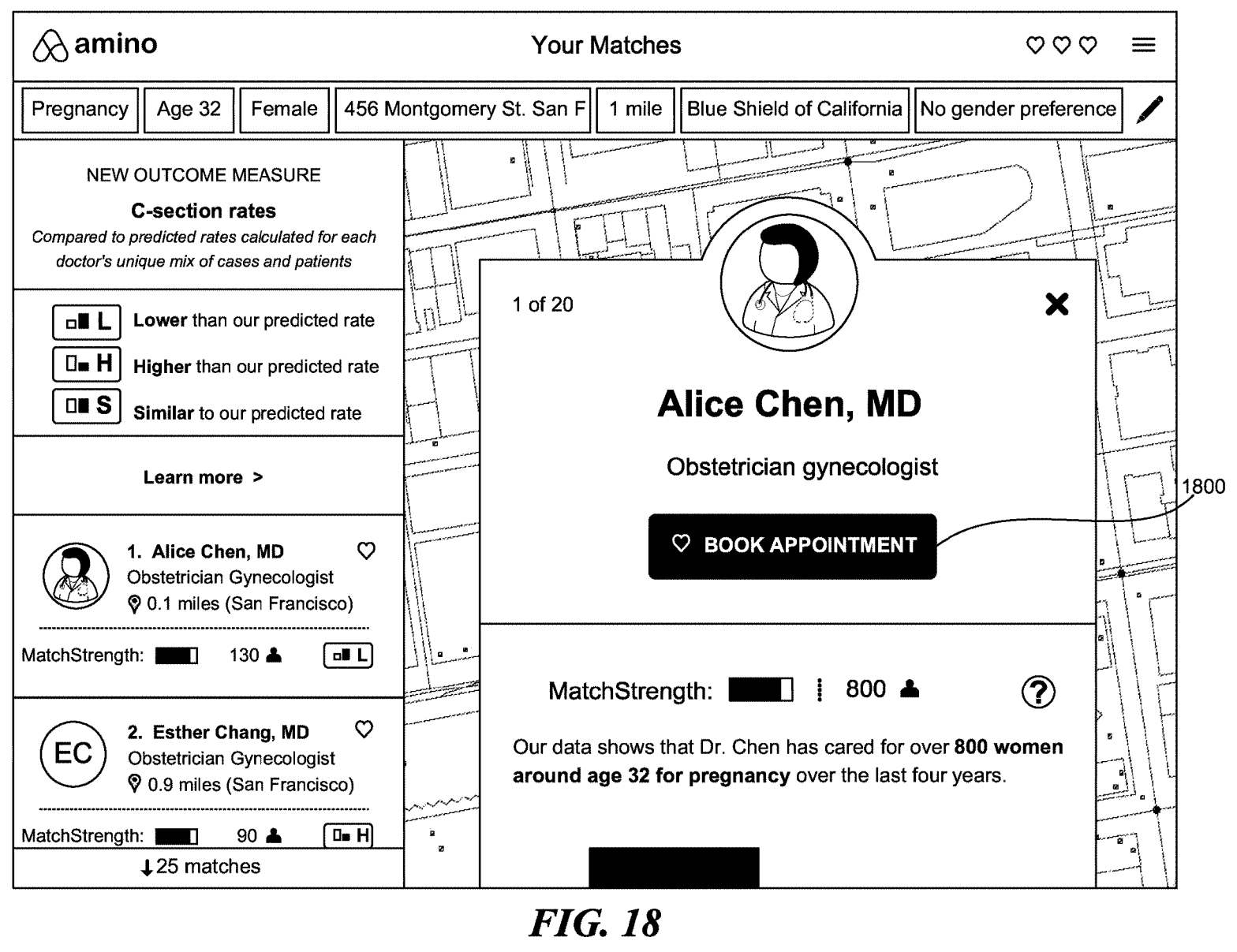

FIG. 18 is a second information tier, according to one embodiment. In this embodiment, the second information tier 67, comprises a display element 1800 configured to schedule an appointment between the healthcare consumer and the healthcare provider of choice.

Computer

Figure 19:
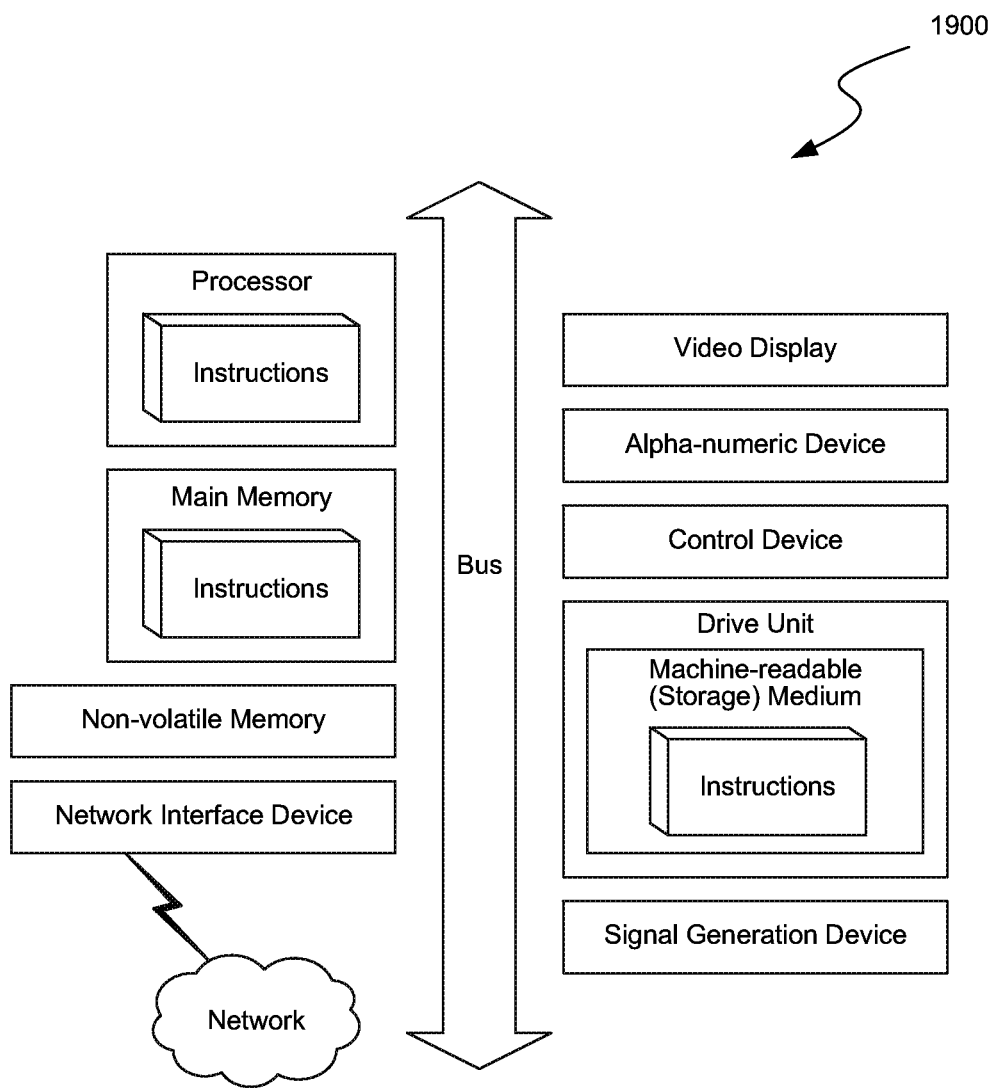
FIG. 19 is a diagrammatic representation of a machine in the example form of a computer system within which a set of instructions, for causing the machine to perform any one or more of the methodologies or modules discussed herein, may be executed.

FIG. 19 is a diagrammatic representation of a machine in the example form of a computer system 1900 within which a set of instructions, for causing the machine to perform any one or more of the methodologies or modules discussed herein, may be executed.

In the example of FIG. 19, the computer system 1900 includes a processor, memory, non-volatile memory, and an interface device. Various common components (e.g., cache memory) are omitted for illustrative simplicity. The computer system 1900 is intended to illustrate a hardware device on which any of the components described in the example of FIGS. 1-18 (and any other components described in this specification) can be implemented. The computer system 1900 can be of any applicable known or convenient type.

The components of the computer system 1900 can be coupled together via a bus or through some other known or convenient device.

This disclosure contemplates the computer system 1900 taking any suitable physical form. As example and not by way of limitation, computer system 1900 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, computer system 1900 may include one or more computer systems 1900; be unitary or distributed; span multiple locations; span multiple machines; or reside in a cloud, which may include one or more cloud components in one or more networks. Where appropriate, one or more computer systems 1900 may perform without substantial spatial or temporal limitation one or more steps of one or more methods described or illustrated herein. As an example and not by way of limitation, one or more computer systems 1900 may perform in real time or in batch mode one or more steps of one or more methods described or illustrated herein. One or more computer systems 1900 may perform at different times or at different locations one or more steps of one or more methods described or illustrated herein, where appropriate.

The processor may be, for example, a conventional microprocessor such as an Intel Pentium microprocessor or Motorola power PC microprocessor. One of skill in the relevant art will recognize that the terms "machine-readable (storage) medium" or "computer-readable (storage) medium" include any type of device that is accessible by the processor.

The memory is coupled to the processor by, for example, a bus. The memory can include, by way of example but not limitation, random access memory (RAM), such as dynamic RAM (DRAM) and static RAM (SRAM). The memory can be local, remote, or distributed.

The bus also couples the processor to the non-volatile memory and drive unit. The non-volatile memory is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software in the computer 1900. The non-volatile storage can be local, remote, or distributed. The non-volatile memory is optional because systems can be created with all applicable data available in memory. A typical computer system will usually include at least a processor, memory, and a device (e.g., a bus) coupling the memory to the processor.

Software is typically stored in the non-volatile memory and/or the drive unit. Indeed, storing and entire large program in memory may not even be possible. Nevertheless, it should be understood that for software to run, if necessary, it is moved to a computer readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium." A processor is considered to be "configured to execute a program" when at least one value associated with the program is stored in a register readable by the processor.

The bus also couples the processor to the network interface device. The interface can include one or more of a modem or network interface. It will be appreciated that a modem or network interface can be considered to be part of the computer system 1900. The interface can include an analog modem, isdn modem, cable modem, token ring interface, satellite transmission interface (e.g., "direct PC"), or other interfaces for coupling a computer system to other computer systems. The interface can include one or more input and/or output devices. The I/O devices can include, by way of example but not limitation, a keyboard, a mouse or other pointing device, disk drives, printers, a scanner, and other input and/or output devices, including a display device. The display device can include, by way of example but not limitation, a cathode ray tube (CRT), liquid crystal display (LCD), or some other applicable known or convenient display device. For simplicity, it is assumed that controllers of any devices not depicted in the example of FIG. 9 reside in the interface.

In operation, the computer system 1900 can be controlled by operating system software that includes a file management system, such as a disk operating system. One example of operating system software with associated file management system software is the family of operating systems known as Windows® from Microsoft Corporation of Redmond, Wash., and their associated file management systems. Another example of operating system software with its associated file management system software is the Linux™ operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "generating" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may thus be implemented using a variety of programming languages.

In alternative embodiments, the machine operates as a standalone device or may be connected (e.g., networked) to other machines. In a networked deployment, the machine may operate in the capacity of a server or a client machine in a client-server network environment, or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies or modules of the presently disclosed technique and innovation.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and storage of charge or a release of stored charge. Likewise, in other memory devices, a change of state may comprise a physical change or transformation in magnetic orientation or a physical change or transformation in molecular structure, such as from crystalline to amorphous or vice versa. The foregoing is not intended to be an exhaustive list of all exam page on ples in which a change in state for a binary one to a binary zero or vice-versa in a memory device may comprise a transformation, such as a physical transformation. Rather, the foregoing is intended as illustrative examples.

A storage medium typically may be non-transitory or comprise a non-transitory device. In this context, a non-transitory storage medium may include a device that is tangible, meaning that the device has a concrete physical form, although the device may change its physical state. Thus, for example, non-transitory refers to a device remaining tangible despite this change in state.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling others skilled in the relevant art to understand the claimed subject matter, the various embodiments, and the various modifications that are suited to the particular uses contemplated.

While embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Although the above Detailed Description describes certain embodiments and the best mode contemplated, no matter how detailed the above appears in text, the embodiments can be practiced in many ways. Details of the systems and methods may vary considerably in their implementation details, while still being encompassed by the specification. As noted above, particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless those terms are explicitly defined herein. Accordingly, the actual scope of the invention encompasses not only the disclosed embodiments, but also all equivalent ways of practicing or implementing the embodiments under the claims.

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which is set forth in the following claims.

The invention claimed is:

1. A computer-implemented method for presenting information to a healthcare consumer on a handheld mobile device, including a display device, by progressively presenting context-based questions and presenting information associated with a ranked list of suggested healthcare providers on a graphical user interface on said display device, said method comprising:
receiving, from a database, a healthcare provider information associated with a healthcare provider of a plurality of healthcare providers;
causing said handheld mobile device to generate said graphical user interface on said display device, said graphical user interface comprising a number of a plurality of context-based questions as an overlapping sequence of a stack of cards,
wherein each card is associated with a single question such that a number of said stack of cards corresponds to said number of said plurality of context-based questions,
wherein an indication of a remaining number of said plurality of context-based questions is displayed on said display device as a remaining number of said stack of cards that are partially visible on said graphical user interface,
wherein said number of said plurality of context-based questions is formulated based on information required to calculate said ranked list of suggested healthcare providers, and
wherein said remaining number of said plurality of context-based questions depends on answers input by said healthcare consumer via said handheld mobile device to respond to said plurality of context-based questions;
receiving, from said handheld mobile device, a first answer to a first context-based question of said plurality of context-based questions, said first context-based question regarding a health issue associated with said healthcare consumer;
receiving, from said handheld mobile device, a second answer to a second context-based question of said plurality of context-based questions,
wherein said second context-based question is formulated based on said healthcare provider information and said first answer, and
wherein each subsequent context-based question and a current quantity of said stack of cards is formulated dynamically based on previously received answers;
calculating said ranked list of suggested healthcare providers based on at least said first answer, said second answer, and said healthcare provider information;
sending, to said handheld mobile device, said ranked list of suggested healthcare providers,
wherein said ranked list comprises a plurality of items representing a first information tier associated with said healthcare provider and a first display element configured to receive a first consumer selection, and
wherein said first information tier comprises a graphic representing a match strength between said consumer and said healthcare provider and a text representing a number of similar consumers that said healthcare provider has treated;
upon receiving said first consumer selection:
sending, to said handheld mobile device, a second information tier associated with said healthcare provider, and
causing display, on said display device, of a second display element configured to receive a second consumer selection,
wherein said second information tier comprises a graphic comparison between a number of similar healthcare consumers said healthcare provider has treated and an average number of similar healthcare consumers other healthcare providers have treated; and
upon receiving said second consumer selection:
sending, to said handheld mobile device, a third information tier associated with said healthcare provider, and
causing display, on said display device, a third display element configured to receive a third consumer selection, said third information tier comprising a graphical representation of a percentage breakdown of different health issues said healthcare provider has treated.

2. The method of claim 1 further comprising:
sending, to said handheld mobile device, a list of suggested answers to said first question based on said healthcare provider information.

3. The method of claim 1, wherein said first information tier further comprises a graphic comparison between a frequency associated with a relevant procedure performed by said healthcare provider and an average frequency associated with said relevant procedure performed by other healthcare providers, and wherein said relevant procedure comprises a procedure associated with said health issue.

4. The method of claim 1, wherein said healthcare provider information comprises a number of similar healthcare consumers that said healthcare provider has treated, wherein said similar healthcare consumers comprise healthcare consumers of similar age as said healthcare consumer and a health issue related to said healthcare consumer.

5. The method of claim 1 further comprising:
storing said first answer and said second answer in a profile associated with said healthcare consumer.

6. The method of claim 1, wherein said first context-based question and said second context-based question belong to a category of comprising a health issue associated with said healthcare consumer, an age associated with said healthcare consumer, a gender associated with said healthcare consumer, an insurance associated with said healthcare consumer, a location associated with said healthcare consumer, a distance said healthcare consumer is willing to travel, and a preference for a gender of a healthcare provider.

7. The method of claim 1, wherein said healthcare provider information comprises a percentage breakdown of different health issues that said healthcare provider has treated and an average distance that healthcare consumers associated with said healthcare provider travel to meet with said healthcare provider.

8. The method of claim 1 further comprising:
along with said first context-based question and said second context-based question, sending to said handheld mobile device a visual guide indicating said remaining number of said plurality of context-based questions.

9. The method of claim 1 further comprising:
upon receiving a third healthcare consumer selection, sending to said handheld mobile device a fourth information tier associated with said healthcare provider and a fourth display element configured to receive a fourth healthcare consumer selection, said fourth information tier comprising a graphic comparison between a frequency associated with a procedure performed by said healthcare provider and an average frequency associated with said procedure performed by other healthcare providers.

10. The method of claim 1, wherein said first information tier further comprises:
a graphic badge indicating that said healthcare provider treats more healthcare consumers than 99% of other healthcare providers associated in a common specialty, and
a graphic comparison between a frequency associated with a relevant procedure performed by said healthcare provider and an average frequency associated with said relevant procedure performed by other healthcare providers, wherein said relevant procedure comprises a procedure associated with said health issue.

11. The method of claim 1, wherein said ranked list further comprises a visual representation associated with said healthcare provider.

12. The method of claim 1, wherein said first display element comprises said item associated with said ranked list.

13. The method of claim 1, wherein said third information tier further comprises success rates associated with treatments.

14. The method of claim 1, further comprising:
displaying, on said display device, a display element configured to make an appointment with a selected healthcare provider.

15. The method of claim 1, further comprising:
receiving, from said handheld mobile device, a geolocation information associated with said handheld mobile device;
based on said geolocation information and said healthcare provider information, sending to said handheld mobile device a list of suggested answers to said first context-based question.

16. The method of claim 1, wherein said ranked list comprising a plurality of items representing a summary of information associated with a particular healthcare provider, wherein each item represents a summary of information comprises a graphic representing a match strength between said healthcare consumer and said particular healthcare provider, and a text representing a number of similar healthcare consumers that said healthcare provider has treated.

17. The method of claim 1, wherein said similar healthcare consumers comprise healthcare consumers of similar age as said healthcare consumer, similar health issue as said healthcare consumer, and same gender as said healthcare consumer.

18. A computer-implemented method for enabling a handheld mobile device, including a display device, associated with a healthcare consumer to control and interface with a remote healthcare database and a remote healthcare server while preserving healthcare consumer privacy, said method comprising:
maintaining said healthcare database comprising a healthcare provider information associated with a healthcare provider of a plurality of healthcare providers;
instantiating a healthcare provider discovery process on said healthcare server;
causing instantiation of a healthcare consumer discovery graphical user interface on said display device;
establishing a connection between said handheld mobile device and said healthcare server;
enabling said healthcare consumer to interact with said healthcare database by using said graphical user interface on said display device, said enabling including:
causing display, on said display device, of a sequence of a plurality of context-based questions in an overlapping sequence of a stack of cards,
wherein each of said stack of cards is associated with a single one of said plurality of context-based questions such that a number of said stack of cards corresponds to a number of said plurality of context-based questions,
wherein an indication of a remaining number of said plurality of context-based questions is displayed as a remaining number of said stack of cards that are partially visible on said graphical user interface on said display device,
wherein said number of said plurality of context-based questions is formulated based on information required to calculate a ranked list of suggested healthcare providers, and
wherein said remaining number of said plurality of context-based questions depends on responses by said healthcare consumer to said plurality of context-based questions;
upon receiving an answer to a displayed context-based question from said handheld mobile device, causing said display device to present a next context-based question received from a server,
wherein said next context-based question is formulated based on answers received in response to previous context-based questions, and
wherein a current number of said stack of cards is dynamically formulated based on answers received in responses to previous questions;
displaying, on said display device, information associated with said ranked list of suggested healthcare providers,
wherein said ranked list comprises a plurality of items representing a summary of information associated with a healthcare provider,
wherein each item represents a summary of information comprises a graphic representing a match strength between said healthcare consumer and said healthcare provider, and
wherein a text represents a number of similar healthcare consumers that said healthcare provider has treated; and
based on healthcare consumer input, causing display, on said display device, of additional detailed information associated with a selected healthcare provider.

19. A computer-implemented method for gathering information from a healthcare consumer by using a sequence of context-based questions, and progressively presenting information associated with a ranked list of suggested healthcare providers, said method comprising:

displaying, on a display device of a handheld mobile device, a sequence of a plurality of context-based questions in a sequence of a stack of cards, wherein each of said stack of cards is associated with a single question such that a number of said stack of cards corresponds to a number of said plurality of context-based questions, wherein an indication of a remaining number of said plurality of context-based questions is displayed as a remaining number of said stack of cards that are partially visible on a graphical user interface on said display device, and wherein said number of said plurality of context-based questions is formulated to gather information to calculate said ranked list of suggested healthcare providers, and wherein said remaining number of said plurality of context-based questions depends on responses by said healthcare consumer to said plurality of context-based questions;

upon receiving an answer to a displayed question from said handheld mobile device associated with said healthcare consumer, receiving a next context-based question from a server, wherein said next context-based question is formulated based on answers received in response to previous questions, wherein each subsequent context-based question and a current number of said stack of cards is formulated based on answers received in responses to previous context-based questions;

causing display, on said display device, information associated with a ranked list of suggested healthcare providers, wherein said ranked list comprising a plurality of items representing a summary of information associated with a healthcare provider, wherein each item representing a summary of information comprises a graphic representing a match strength between said healthcare consumer and said healthcare provider, and wherein a text representing a number of similar healthcare consumers said healthcare provider has treated; and based on healthcare consumer input, displaying, on said display device, additional detailed information associated with a selected healthcare provider.

\* \* \* \* \*